United States Patent
Komatsu et al.

(10) Patent No.: US 7,001,749 B2
(45) Date of Patent: Feb. 21, 2006

(54) REGENERATING METHOD OF IMMOBILIZED ENZYME

(75) Inventors: Toshiteru Komatsu, Kashima-gun (JP); Yoshitaka Senda, Kamisu-machi (JP); Goro Ujita, Kashima-gun (JP)

(73) Assignee: Kao Corporation, Tokyo (JP)

( * ) Notice: Subject to any disclaimer, the term of this patent is extended or adjusted under 35 U.S.C. 154(b) by 98 days.

(21) Appl. No.: 10/654,890

(22) Filed: Sep. 5, 2003

(65) Prior Publication Data

US 2004/0126864 A1    Jul. 1, 2004

(30) Foreign Application Priority Data

Sep. 6, 2002    (JP)    ............................. 2002-261256

(51) Int. Cl.
*C12P 7/64*    (2006.01)

(52) U.S. Cl. ...................................... 435/134; 435/198
(58) Field of Classification Search ................ 435/178, 435/174, 134, 180, 177, 198
See application file for complete search history.

(56) References Cited

U.S. PATENT DOCUMENTS 4,629,742 A    12/1986    Brady et al.

FOREIGN PATENT DOCUMENTS

| | | |
|---|---|---|
| EP | 0 320 132 | 6/1989 |
| EP | 1 008 647 | 6/2000 |
| JP | 5-137574 | 6/1993 |
| JP | 9-56379 | 3/1997 |
| JP | 11-75834 | 3/1999 |

OTHER PUBLICATIONS

F. X. Malcata, et al., 3rd International Conference on Effective Membrane Processes, XP-008024234, pp. 107-122, "Hydrolysis of Butteroil by Immobilized Lipase in a Hollow Fiber Membrane Reactor: Optimization and Economic Considerations", Jan. 1993.

V. M. Balcao, et al., Enzyme and Microbial Technology, vol. 18, No. 18, XP-001070652, pp. 392-416, "Bioreactors with Immobilized Lipases: State of the Art", May 1, 1996.

*Primary Examiner*—Jean C. Witz
*Assistant Examiner*—Satyendra K. Singh
(74) *Attorney, Agent, or Firm*—Oblon, Spivak, McClelland, Maier & Neustadt, P.C.

(57) ABSTRACT

Provided is a method for regenerating an immobilized enzyme for lipolysis which has been used for lipolysis, thereby exhibiting a reduced activity, which includes washing the immobilized enzyme with a solvent; controlling an equilibrium concentration of fatty acids in the solvent; removing the washed immobilized enzyme therefrom, and contacting the resulting immobilized enzyme with a fresh enzyme, wherein the fresh enzyme adsorbs onto the immobilized enzyme. According to the preferred methods of the present invention, it is possible to make effective use of the residual activity of an immobilized enzyme spent for lipolysis and regenerate the spent immobilized enzyme to have a performance similar to that before the lipolysis at a low cost using less amount of liquid waste.

10 Claims, 1 Drawing Sheet

REGENERATING METHOD OF IMMOBILIZED ENZYME

FIELD OF THE INVENTION

The present invention relates to a method for regenerating an immobilized enzyme for lipolysis after use, and more specifically, a method of making effective use of the residual activity of an immobilized enzyme which has been used for lipolysis and regenerating the used immobilized enzyme.

BACKGROUND OF THE INVENTION

In case of hydrolysis of a fat or oil by using a lipolytic enzyme, an immobilized enzyme wherein a lipolytic enzyme is immobilized onto an inorganic or organic carrier, is employed for efficient use of the enzyme. The activity of this immobilized enzyme lowers as it is used over time during a hydrolysis reaction, and thus the enzyme must be freshly replaced when its activity reaches a certain low level.

For effective use of the immobilized enzyme recovered after use, one can easily conceive a method of removing from the immobilized enzyme all the oils and proteins adhered thereto and using the carrier again. This method however involves such problems in which it is necessary to wash the waste with liquid amounting to several hundred times as much as the amount of the enzyme carrier and thus is environmentally undesirable, and the activity remaining in the immobilized enzyme after use cannot be completely utilized.

In addition, disclosed are a method of eliminating, from an immobilized lipase whose activity has been lowered after being used for ester exchange or ester transfer reaction, factors obstructive to an enzymatic reaction by washing the enzyme with a solvent (Japanese Patent Application Laid-Open No. 137574/1993); and a method of subjecting lipase, which has lost its water content by the reaction under low moisture conditions, to a wetting treatment with a solvent or a mixture of a solvent and a phospholipid, thereby controlling the water content contributing to the reaction and reactivating the remaining lipase (Japanese Patent Application Laid-Open No. 56379/1997, or Japanese Patent Application Laid-Open No. 75834/1999). The above-described methods however do not regenerate an immobilized enzyme whose activity has been lowered by the loss of part of the lipase, but reactivate the remaining lipase.

SUMMARY OF THE INVENTION

In the present invention, there is thus provided a method for regenerating an immobilized enzyme for lipolysis exhibiting a reduced activity as a result of having been used for lipolysis, which includes the steps of washing the immobilized enzyme with a solvent, controlling an equilibrium concentration of fatty acids in the solvent, removing the washed immobilized enzyme therefrom, and contacting the resulting immobilized enzyme with a fresh enzyme, wherein the fresh enzyme adsorbs onto the immobilized enzyme.

DETAILED DESCRIPTION OF THE INVENTION

Figure 1:
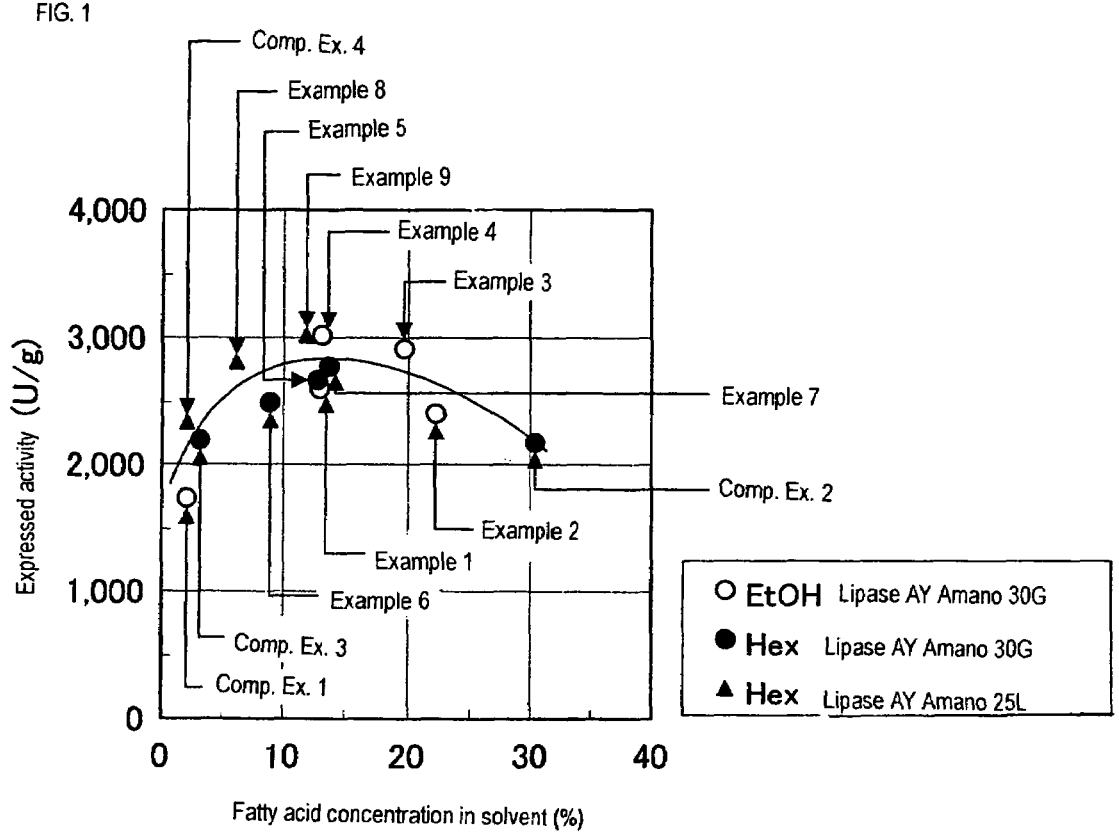
FIG. 1 illustrates the relationship between a concentration of fatty acids in the washing liquid of a spent immobilized enzyme and an expressed activity of a regenerated immobilized enzyme, in the Examples and the Comparative Examples.

All publications cited herein are hereby incorporated by reference.

As used herein "lipolysis" means hydrolysis of fats and oils. A "lipolytic enzyme" means an enzyme for hydrolysis of fats and oils.

The present invention relates to a method of making effective use of the residual activity of an immobilized enzyme which has been used for lipolysis reaction and regenerating the spent immobilized enzyme to have a performance similar to that before use at a low cost while using less amount of liquid waste.

It is known that in case of immobilization of a lipolytic enzyme, a highly active immobilized enzyme is available by preliminarily causing a fatty acid to be adsorbed onto an enzyme carrier (Japanese Patent Application Laid-Open No. 153090/1989). The present inventors have found that an immobilized enzyme which has been used for a lipolysis reaction can be regenerated to have an activity equal to that of a fresh immobilized enzyme advantageously from the viewpoints of environment and economy, by treating the spent immobilized enzyme with a solvent so as not to completely remove a large amount of fatty acids adhered to the spent immobilized enzyme, but to leave an amount of the fatty acids effective for reactivation, and then replenishing the activity of the enzyme by causing a fresh enzyme for lipolysis to be adsorbed onto the resulting immobilized enzyme.

Examples of the carrier for an immobilized enzyme which is to be regenerated by the method of the present invention include inorganic carriers such as celite, diatomaceous earth, kaolinite, silica gel, molecular sieves, porous glass, activated charcoal, calcium carbonate and ceramics; and organic polymers such as polyvinyl alcohols, polypropylenes, chitosan, ion exchange resins, hydrophobic adsorption resins, chelate resins and synthetic adsorption resins, of which the ion exchange resins are particularly preferred.

As the ion exchange resin, a porous anion exchange resin is preferred. Such a porous carrier has a large surface area, enabling an increase in the adsorption amount of an enzyme. The particle size of the resin is preferably from about 100 to 1000 μm, while the pore size is desirably from about 10 to 150 nm. As the material of the resin, phenol-formaldehyde, polystyrene, acrylamide and divinylbenzene are usable. Particularly desired is a phenol-formaldehyde resin (for example, "Duolite A-568", product of Rhom and Haas).

As the lipolytic enzyme to be used in the present invention, lipase is preferred. Not only the lipase derived from animals or plants but also commercially available lipase derived from microorganisms is usable. Examples of the lipase derived from microorganisms include those originated from the genera *Rhizopus, Aspergillus, Mucor, Pseudomonas, Geotrichum, Penicillium,* and *Candida.*

The spent immobilized enzyme which is to be regenerated by the method of the present invention is an immobilized enzyme which has been used for hydrolysis of fat or oil, thereby exhibiting a reduced activity. Examples of the fat or oil include vegetable oils such as soybean oil, olive oil, palm oil and rapeseed oil, and animal oils such as beef tallow, lard and fish oil.

Examples of the solvent to be used for washing of the spent immobilized enzyme include ethanol, n-hexane and acetone, among which ethanol and n-hexane are particularly preferred. Among these, n-hexane is more preferred, because it neither eliminates nor deactivates the remaining enzyme and therefore enables a reduction in the amount of the enzyme to be supplied.

When the spent immobilized enzyme is washed with such a solvent (herein, "washing liquid") for a predetermined period of time (for example, about 30 minutes), the fatty acid concentration in the washing liquid and the amount of the fatty acid remaining in (adsorbed to) the immobilized enzyme come to equilibrium. The fatty acid concentration in the washing liquid is, for example, expressed by the weight of fatty acids dissolved in the unit weight of the washing liquid, while the amount of the fatty acid remaining in the immobilized enzyme is expressed by the weight of the fatty acids per unit weight of the immobilized enzyme. In the present invention, it is necessary to control the equilibrium concentration of the fatty acids in the washing liquid in order to obtain a regenerated immobilized enzyme having a high activity. This equilibrium concentration of the fatty acids may be controlled, as needed, depending on the form of the enzyme to be adsorbed after removal of the washing liquid and preferably ranges from about 4 to 28 wt. %, more preferably from about 5 to 25 wt. %, even more preferably from about 5 to 22 wt. %, and still more preferably from about 5 to 20 wt. %. The amount of the solvent may be adjusted so that the equilibrium concentration of the fatty acids in the washing liquid falls within the above-described range in consideration of the amount of the fatty acid contained in the immobilized enzyme before washing. In general, the amount of the solvent is preferably about 3 to 20 times, more preferably about 3 to 15 times, even more preferably about 3 to 10 times, even more preferably 5 to 10 times, and still more preferably 5 to 8 times, the weight of the spent immobilized enzyme. The washing temperature of the immobilized enzyme with the solvent is adjusted so as not to deactivate the remaining enzyme, and is preferably from about 0 to 60° C., and more preferably from about 5 to 40° C.

After washing with the solvent, the washing liquids are removed by filtration or the like and the immobilized enzyme is washed with a buffer. The remaining solvent is completely removed by this washing with the buffer. Alternatively, the solvent may be removed by distillation. Particularly when the solvent is n-hexane, distillation is preferred. The distillation may be either atmospheric distillation or distillation under reduced pressure. As the buffer, that usable for the immobilization of an enzyme in the subsequent step is preferred.

Although the immobilizing temperature of the enzyme can be determined by the properties of the enzyme, a range of from about 0 to 60° C., especially from about 5 to 40° C. is preferred, because it does not cause deactivation of the enzyme. The pH of the enzyme solution to be used for immobilization should fall within a range not causing modification of the enzyme and the pH can be determined by the properties of the enzyme as in the determination of the immobilizing temperature. Preferred pH ranges from about 3 to 9. A buffer is used for keeping within this pH range. Examples of the buffer include acetate buffers, phosphate buffers and tris-HCl buffers.

The enzyme concentration in the above-described enzyme solution is desirably not greater than a saturated solubility of the enzyme but sufficiently high from the viewpoint of immobilization efficiency. The amount of the enzyme to be adsorbed may be controlled, depending on the residual activity of the spent immobilized enzyme. As the enzyme solution, a supernatant obtained by removing insoluble matters by centrifugal separation or a solution purified by ultrafiltration can be employed as needed.

After immobilization of the enzyme, it is possible to recover the immobilized enzyme in the wet state by filtration and provide it for the subsequent lipolysis reaction. If necessary, water may be removed from the immobilized enzyme by treating it with the fat or oil as described in Japanese Patent Application Laid-Open No. 166552/2000 or by drying it.

The activity (1U) of the immobilized enzyme means a decomposition capacity of the enzyme capable of generating 1 $\mu$mol of free fatty acids per minute when hydrolysis is performed for 30 minutes by mixing it with a 100:25 (parts by weight) mixture of a fat or oil and water at 40° C. under stirring.

The following examples further describe and demonstrate embodiments of the present invention. The examples are given solely for the purpose of illustration and are not to be construed as limitations of the present invention.

EXAMPLES

Preparation of Spent Immobilized Enzyme

In 100 parts by weight of an N/10 aqueous sodium hydroxide solution, 10 parts by weight of "Duolite A-568" (trade name; product or Rohm and Hass) was stirred for 1 hour. After filtration, the "Duolite A-568" was washed with 100 parts by weight of deionized water, followed by pH equilibration with 100 parts by weight of a 500 mM phosphate buffer (pH 7). The pH equilibration was then conducted twice, each for 2 hours with 100 parts by weight of a 50 mM phosphate buffer (pH 7). The carrier was then recovered by filtration, followed by ethanol substitution with 40 parts by weight of ethanol. After filtration, a mixture of 10 parts by weight of ricinoleic acid and 31.6 parts by weight of ethanol was added to the carrier and ricinoleic acid was caused to be adsorbed onto the carrier for 30 minutes. The carrier was then recovered and washed 4 times, each for 30 minutes with 50 parts by weight of a 50 mM phosphate buffer (pH 7), to remove the ethanol. The carrier was collected by filtration. Immobilization of an enzyme was then performed by bringing the carrier into contact with an enzyme solution obtained by dissolving 3.88 parts by weight of lipase ("Lipase AY Amano 30", trade name; product of Amano Enzyme Inc.) in 180 parts by weight of a 50 mM phosphate buffer (pH7) for 2 hours. At this time, the immobilization ratio was determined from the difference between the residual activity of the enzyme solution after immobilization and the activity of the enzyme solution before immobilization, and was 70%. After recovery of the immobilized enzyme by filtration after immobilization, it was washed with 50 parts by weight of a 50 mM phosphate buffer (pH 7) for 30 minutes to remove the enzyme and proteins which had not been immobilized. By filtration after washing, the immobilized enzyme was recovered in the wet state. The immobilized enzyme thus recovered and 40 parts by weight of a rapeseed oil were brought into contact with each other for 2 hours, followed by filtration, whereby an oil-treated immobilized enzyme was recovered. The above-described procedures were all carried out at 20° C.

The expressed activity of the immobilized enzyme thus prepared by the above-described procedures was initially 2,800 U/g. The immobilized enzyme was filled in a column and hydrolysis was successively repeated by mixing it with a reaction substrate (rapeseed oil: water=100 parts by weight: 60 parts by weight) circulated in the column. As the hydrolysis was repeated, the activity of the enzyme lowered. In this manner, spent immobilized enzymes (enzymes exhibiting reduced activity) having various residual activities were recovered.

Example 1

Ethanol (72 parts by weight) was added to 10 parts by weight (dry weight) of a spent immobilized enzyme having a residual activity of 770 U/g to disperse the immobilized enzyme in the ethanol. The resulting dispersion was stirred for 30 minutes. The fatty acid concentration in the washing liquid after stirring was 12.9 wt. %. After filtration, the immobilized enzyme was washed four times, each with 50 parts by weight of a 50 mM phosphate buffer (pH 7) for 30 minutes, to remove ethanol and the residue was filtered to recover the immobilized enzyme. Then, the immobilized enzyme was brought into contact with an enzyme solution obtained by dissolving 3.88 parts by weight of lipase ("Lipase AY Amano 30", trade name; product of Amano Enzyme Inc.) in 180 parts by weight of a 50 mM phosphate buffer (pH 7) for 2hours to immobilize the enzyme onto the immobilized enzyme. The immobilization ratio at this time was determined from the difference between the residual activity of the enzyme solution after immobilization and the activity of the enzyme solution before immobilization, and was found to be 67%. After recovery of the immobilized enzyme by filtration, it was washed with 50 parts by weight of a 50 mM phosphate buffer (pH 7) for 30 minutes to remove the enzyme and proteins which had not been immobilized. By filtration after washing, the immobilized enzyme was recovered in the wet state. The above-described procedures were all carried out at 20° C.

The expressed activity of the immobilized enzyme thus regenerated by the above-described procedures was initially 2,600 U/g.

Example 2

In a manner similar to that in Example 1 except that ethanol was added in an amount of 40 parts by weight, an immobilized enzyme was regenerated. As a result, the fatty acid concentration in the washing liquid was 22.3 wt. %, the immobilization ratio of the enzyme was 73.1% and the expressed activity of the immobilized enzyme after regeneration was 2,401 U/g.

Example 3

In a manner similar to that in Example 1 except that a spent immobilized enzyme had a residual activity of 800 U/g and ethanol was added in an amount of 40 parts by weight, an immobilized enzyme was regenerated. As a result, the fatty acid concentration in the washing liquid was 19.7 wt. %, the immobilization ratio of the enzyme was 70.9% and the expressed activity of the immobilized enzyme after regeneration was 2,910 U/g.

Example 4

In a manner similar to that in Example 1 except that a spent immobilized enzyme had a residual activity of 1,440 U/g and ethanol was added in an amount of 72 parts by weight, an immobilized enzyme was regenerated. As a result, the fatty acid concentration in the washing liquid was 13.1 wt. %, the immobilization ratio of the enzyme was 69.6% and the expressed activity of the immobilized enzyme after regeneration was 3,014 U/g.

Example 5

In a manner similar to that in Example 1 except that a spent immobilized enzyme was dispersed in n-hexane in place of ethanol, and stirring was conducted for 30 minutes. At this time, the fatty acid concentration in the solvent after stirring was 12.8 wt. %. After filtration, 50 parts by weight of a 50 mM phosphate buffer (pH 7) was poured into the immobilized enzyme, the resulting mixture was stirred for 30 minutes at 20° C. under reduced pressure of 30 Torr, and the solvent was removed. After filtration, the immobilized enzyme was washed three times, each for 30 minutes with 50 parts by weight of a 50 mM phosphate buffer (pH 7), and the immobilized enzyme was recovered by filtration. Then, the lipase was caused to be adsorbed onto the immobilized enzyme as in Example 1. As a result, the immobilization ratio of the enzyme was 70% and the expressed activity of the immobilized enzyme after regeneration was 2,672 U/g.

Example 6

In a manner similar to that in Example 5 except that n-hexane was added in an amount of 110 parts by weight, an immobilized enzyme was regenerated. As a result, the fatty acid concentration in the washing liquid was 8.9 wt. %, the immobilization ratio of the enzyme was 81.4% and the expressed activity of the immobilized enzyme after regeneration was 2,489 U/g.

Example 7

In a manner similar to that in Example 5 except that a spent immobilized enzyme had a residual activity of 1,440 U/g and n-hexane was added in an amount of 68 parts by weight, the immobilized enzyme was regenerated. As a result, the fatty acid concentration in the washing liquid was 13.7 wt. %, the immobilization ratio of the enzyme was 67.5% and the expressed activity of the immobilized enzyme after regeneration was 2,768 U/g.

Example 8

In a manner similar to that employed in Example 5 except that a spent immobilized enzyme had a residual activity of 605 U/g; n-hexane was added in an amount of 182 parts by weight; and the immobilized enzyme was brought into contact with an enzyme solution, which had been obtained by dissolving 36.8 parts by weight of lipase ("Lipase AY Amano 25L", trade name; product of Amano Enzyme Inc.) in 148 parts by weight of a 50 mM phosphate buffer (pH 7), for 2 hours to immobilize the enzyme solution onto the immobilized enzyme, the immobilized enzyme was regenerated. As a result, the fatty acid concentration in the washing liquid was 6.0 wt. %, the immobilization ratio of the enzyme was 81.8% and the expressed activity of the immobilized enzyme after regeneration was 2,814 U/g.

Example 9

In a manner similar to that in Example 8 except that a spent immobilized enzyme had a residual activity of 604 U/g and n-hexane was added in an amount of 89 parts by weight, the immobilized enzyme was regenerated. As a result, the fatty acid concentration in the washing liquid was 11.7 wt %, the immobilization ratio of the enzyme was 76.3% and the expressed activity of the immobilized enzyme after regeneration was 3,016 U/g.

Comparative Example 1

In a manner similar to that in Example 1 except that a spent immobilized enzyme had a residual activity of 700 U/g and ethanol was added in an amount of 530 parts by weight, the immobilized enzyme was regenerated. As a result, the fatty acid concentration in the washing liquid was 2 wt. %, the immobilization ratio of the enzyme was 81.8% and the expressed activity of the immobilized enzyme after regeneration was 1,744 U/g.

Comparative Example 2

In a manner similar to that in Example 5 except that n-hexane was added in an amount of 24 parts by weight, an immobilized enzyme was regenerated. As a result, the fatty acid concentration in the washing liquid was 30.4 wt. %, the immobilization ratio of the enzyme was 59.8% and the expressed activity of the immobilized enzyme after regeneration was 2,167 U/g.

Comparative Example 3

In a manner similar to Example 5 except that n-hexane was added in an amount of 337 parts by weight, an immobilized enzyme was regenerated. As a result, the fatty acid concentration in the washing liquid was 3.1 wt. %, the immobilization ratio of the enzyme was 83.8% and the expressed activity of the immobilized enzyme after regeneration was 2,200 U/g.

Comparative Example 4

In a manner similar to that employed in Example 8 except that a spent immobilized enzyme had a residual activity of 607 U/g and n-hexane was added in an amount of 552 parts by weight, the immobilized enzyme was regenerated. As a result, the fatty acid concentration in the washing liquid was 2.0 wt. %, the immobilization ratio of the enzyme was 79.0% and the expressed activity of the immobilized enzyme after regeneration was 2,334 U/g.

The relation between the fatty acid concentration in the washing liquid of the spent immobilized enzyme and the expressed activity of the regenerated immobilized enzyme, in each of the Examples and the Comparative Examples, is shown in FIG. 1.

What is claimed is:

1. A method for regenerating an immobilized enzyme for lipolysis which exhibits a reduced activity after having been used for lipolysis, which comprises the steps of
    (a) washing the immobilized enzyme comprising fatty acids with a solvent;
    (b) controlling an equilibrium concentration of the fatty acids in the solvent;
    (c) removing the washed immobilized enzyme therefrom, and
    (d) contacting the resulting immobilized enzyme with a fresh enzyme, wherein the fresh enzyme adsorbs onto the immobilized enzyme
    wherein the equilibrium concentration of the fatty acids in the washing liquid is adjusted to fall within a range of from about 4 to 28 wt. %.

2. The method of claim 1, wherein the solvent is selected from the group consisting of ethanol, n-hexane, and mixtures thereof.

3. The method of claim 1, wherein said immobilized enzyme is immobilized on an ion exchange resin having a particle size of about 100 to 1000 $\mu$m and a pore size of about 10 to 150 nm.

4. The method of claim 1, wherein said immobilized enzyme for lipolysis exhibits a reduced activity as a result of use for hydrolysis of fat or oil.

5. The method of claim 1, wherein said solvent is n-hexane.

6. The method of claim 1, wherein said equilibrium concentration is adjusted to fall within a range of 5 to 25 wt. %.

7. The method of claim 1, wherein said equilibrium concentration is adjusted to fall within a range of 5 to 22 wt. %.

8. The method of claim 1, wherein said equilibrium concentration is adjusted to fall within a range of 5 to 20 wt. %.

9. The method of claim 1, wherein washing is conducted at a temperature of from 0 to 60° C.

10. The method of claim 1, wherein washing is conducted at a temperature of from 5 to 40° C.

* * * * *

UNITED STATES PATENT AND TRADEMARK OFFICE
CERTIFICATE OF CORRECTION

PATENT NO. : 7,001,749 B2
APPLICATION NO. : 10/654890
DATED : Feb. 21, 2006
INVENTOR(S) : Komatsu et al.

It is certified that error appears in the above-identified patent and that said Letters Patent is hereby corrected as shown below:

On the title page, Item (75), the second inventor's city of residence is incorrect. Item (75) should read:

-- (75)　Inventors:　　Toshiteru Komatsu, Kashima-gun (JP);
　　　　　　　　　　　Yoshitaka Senda, Kashima-gun (JP);
　　　　　　　　　　　Goro Ujita, Kashima-gun (JP)　--

Signed and Sealed this

First Day of August, 2006

JON W. DUDAS
*Director of the United States Patent and Trademark Office*